United States Patent [19]
Rello

[11] Patent Number: 5,779,209
[45] Date of Patent: Jul. 14, 1998

[54] POSITIONING UNIT

[75] Inventor: Michael J. Rello, Harleysville, Pa.

[73] Assignee: Robert G. Johnston, Medford Lakes, N.J.; a part interest

[21] Appl. No.: 867,130

[22] Filed: Jun. 2, 1997

[51] Int. Cl.[6] ..................................................... E04G 3/00
[52] U.S. Cl. ........................................................ 248/278.1
[58] Field of Search ........................... 248/278.1, 280.11, 248/281.11, 276.1

[56] References Cited

U.S. PATENT DOCUMENTS

| 3,243,497 | 3/1966 | Kendall et al. | 248/278.1 X |
|---|---|---|---|
| 4,545,555 | 10/1985 | Koch | 248/280.11 |
| 4,863,133 | 9/1989 | Bonnell | 278/280.11 |
| 5,538,214 | 7/1996 | Sinila | 248/278.1 |

OTHER PUBLICATIONS

Brochure entitled, "*Instrument Control –manageble and tireless–*," published by Leonard Medical, Inc. Apr., 1993, 7 pages.

*Primary Examiner*—Ramon O. Ramirez
*Attorney, Agent, or Firm*—Ratner & Prestia

[57] ABSTRACT

A positioning unit having two arms and three joints whereby a payload carried by the positioning unit at one of the joints can be moved into a desired position. Each joint has locking and releasing means by which the arms can be moved when the locking and releasing means are released and maintained in a desired position when the locking and releasing means are locked. The locking and releasing of the joints is controlled by two controllers both of which can be actuated simultaneously by a single human hand.

9 Claims, 7 Drawing Sheets

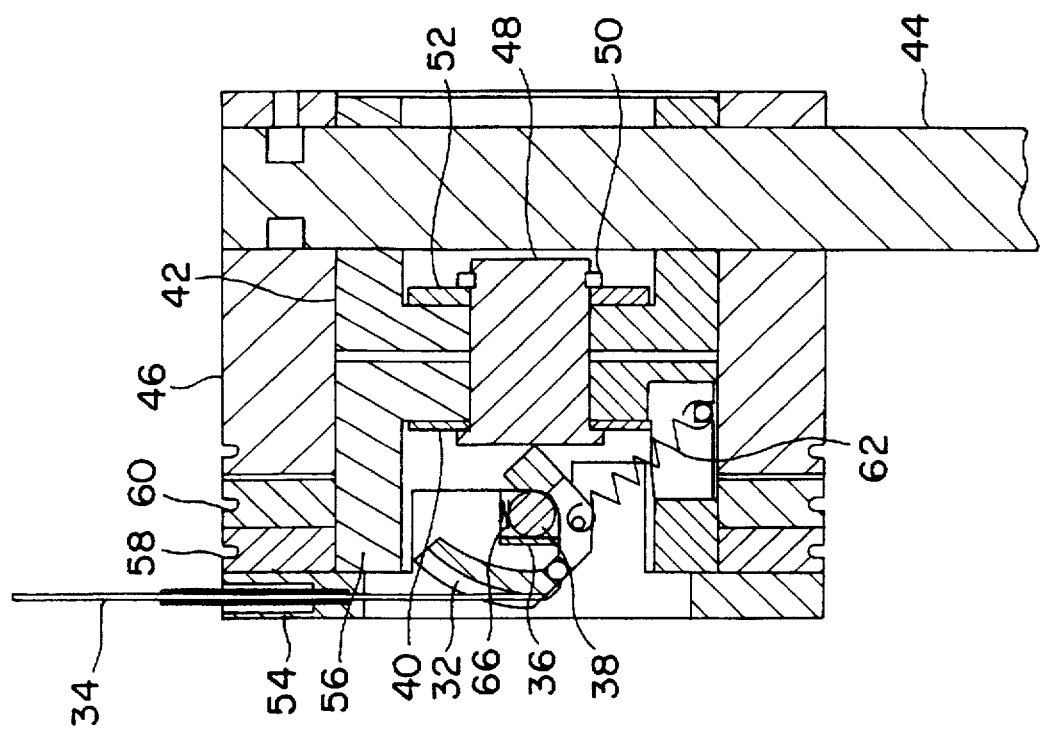
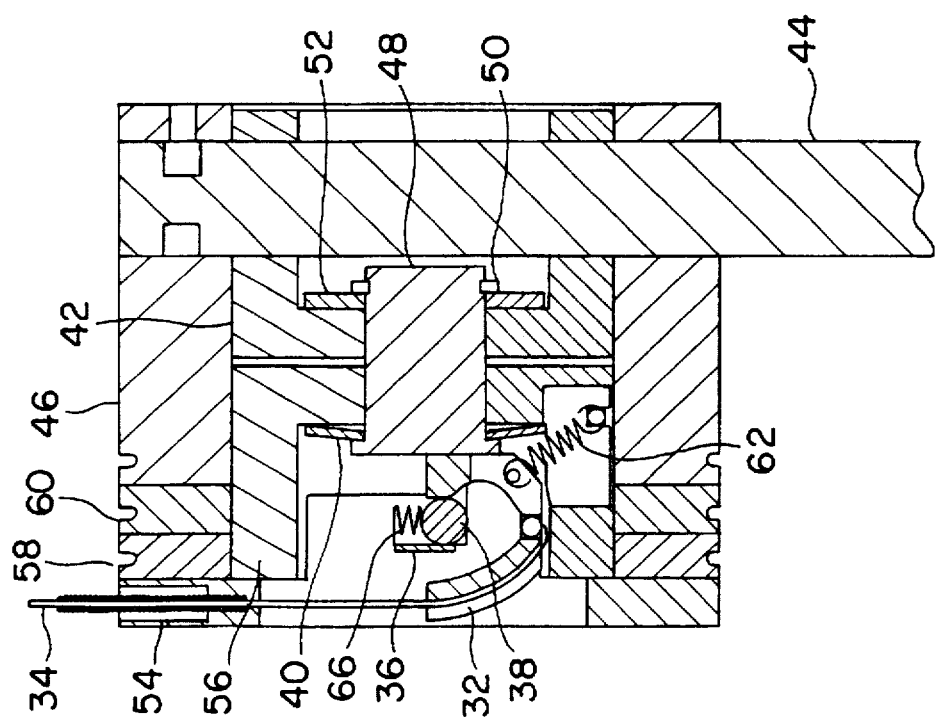

1

POSITIONING UNIT

TECHNICAL FIELD

The present invention relates, in general, to a positioning unit for moving a payload to a desired position and maintaining the payload at the desired position and, in particular, to positioning a medical ultrasound probe against or within a human body and fixing the ultrasound probe in place while a body part is imaged.

BACKGROUND OF THE INVENTION

It is important, in conducting medical ultrasound diagnostic procedures (i.e. imaging human body parts), to minimize, most preferably eliminate, relative movement between the patient under examination and the ultrasound probe which scans the body part of interest of the patent and develops signals from which images are produced. Typically, in order to obtain the desired, accurate images, the patient is restrained against movement during the diagnostic procedure and the individual conducting the diagnostic procedure is required to maintain the ultrasound probe in fixed position against or within the body of the patient. Achieving this result, namely minimizing or eliminating relative movement between the patient and the ultrasound probe, can be very difficult.

Thus, there is the need for a positioning unit for moving an ultrasound probe to a desired position against or within a human body and maintaining the position of the ultrasound probe while a human body part is being imaged. Such a positioning unit preferably should have a plurality of separately selectable degrees of movement and be capable of quickly and easily moving the ultrasound probe to the desired position by the individual positioning the ultrasound probe using only one hand for movements of the positioning unit, while allowing the second hand to move the ultrasound probe to the general region of interest and maintaining the ultrasound probe fixed in the desired position.

SUMMARY OF THE INVENTION

A positioning unit, constructed in accordance with the present invention, includes mounting means for mounting the positioning unit to a stationary surface and first and second arms. Also included in this positioning unit are control means for controlling, upon actuation by a single human hand: (a) locking of the first arm and the second arm against movement of the first arm and the second arm and (b) selective releasing of the first arm and the second arm to permit movement of the first arm and the second arm. A positioning unit, constructed in accordance with the present invention, also includes a first joint for coupling the first arm to the mounting means for: (a) rotational movement of the first arm relative to the mounting means about a first vertical axis and (b) pivotal movement of the first arm relative to the mounting means about a first horizontal axis. The first joint has first locking and releasing means for: (a) preventing: (1) rotational movement of the first arm relative to the mounting means about the first vertical axis and (2) pivotal movement of the first arm relative to the mounting means about the first horizontal axis and (b) selectively permitting: (1) rotational movement of the first arm relative to the mounting means about the first vertical axis and (2) pivotal movement of the first arm relative to the mounting means about the first horizontal axis. A positioning unit, constructed in accordance with the present invention, further includes a second joint for coupling a payload to the second arm for: (a) pivotal movement of the payload relative to the second arm about a

2 second horizontal axis and (b) rotational movement of the payload relative to the second arm about an axis perpendicular to the second horizontal axis. The second joint has second locking and releasing means for: (a) preventing: (1) pivotal movement of the payload relative to the second arm about the second horizontal axis and (2) rotational movement of the payload relative to the second arm about the axis perpendicular to the second horizontal axis and (b) selectively permitting: (1) pivotal movement of the payload relative to the second arm about the second horizontal axis and (2) rotational movement of the payload relative to the second arm about the axis perpendicular to the second horizontal axis. A positioning unit, constructed in accordance with the present invention, further includes a third joint at which the first arm and the second arm are coupled together for relative pivotal movement between the first arm and the second arm about a third horizontal axis and having third locking and releasing means for: (a) preventing relative pivotal movement between the first arm and the second arm about the third horizontal axis and (b) selectively permitting relative pivotal movement between the first arm and the second arm about the third horizontal axis. Also included in this positioning unit are connecting means for connecting the control means to: (a) the first locking and releasing means to: (1) release the first locking and releasing means upon actuation of the control means and (2) lock the first locking and releasing means upon deactuation of the control means, (b) the second locking and releasing means to: (1) release the second locking and releasing means upon actuation of the control means and (2) lock the second locking and releasing means upon deactuation of the control means, and (c) the third locking and releasing means to: (1) release the third locking and releasing means upon actuation of the control means and (2) lock the third locking and releasing means upon deactuation of the control means.

BRIEF DESCRIPTION OF THE DRAWINGS

FIGS. 4A and 4B are sectional views of a first joint of the FIG. 1 positioning unit in the locked condition and the released condition, respectively.

DETAILED DESCRIPTION OF THE INVENTION

Figure 1:
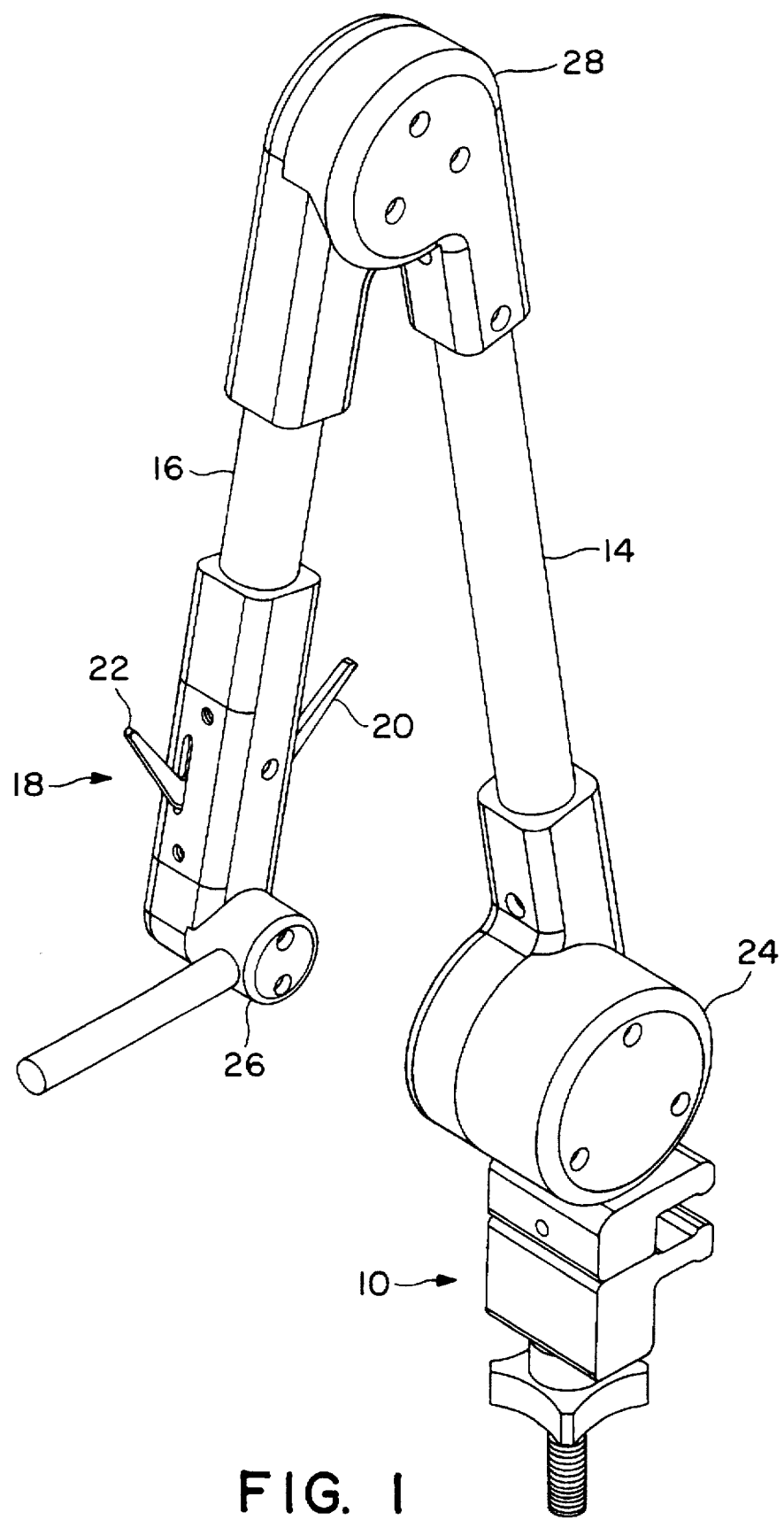
FIG. 1 is a perspective view of a positioning unit constructed in accordance with the present invention.
Figure 2:
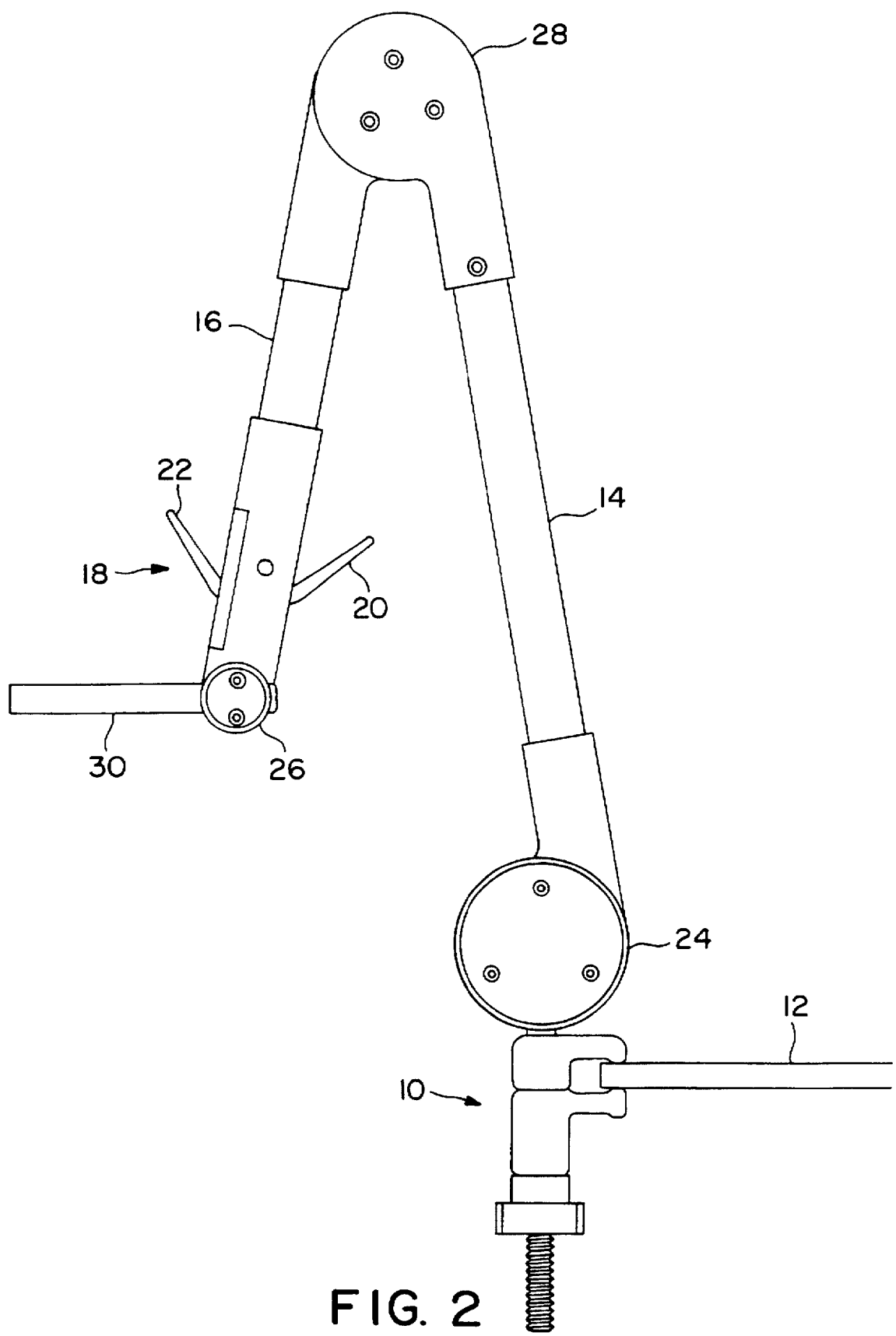
FIG. 2 is a side view of the FIG. 1 positioning unit.
Figure 3:
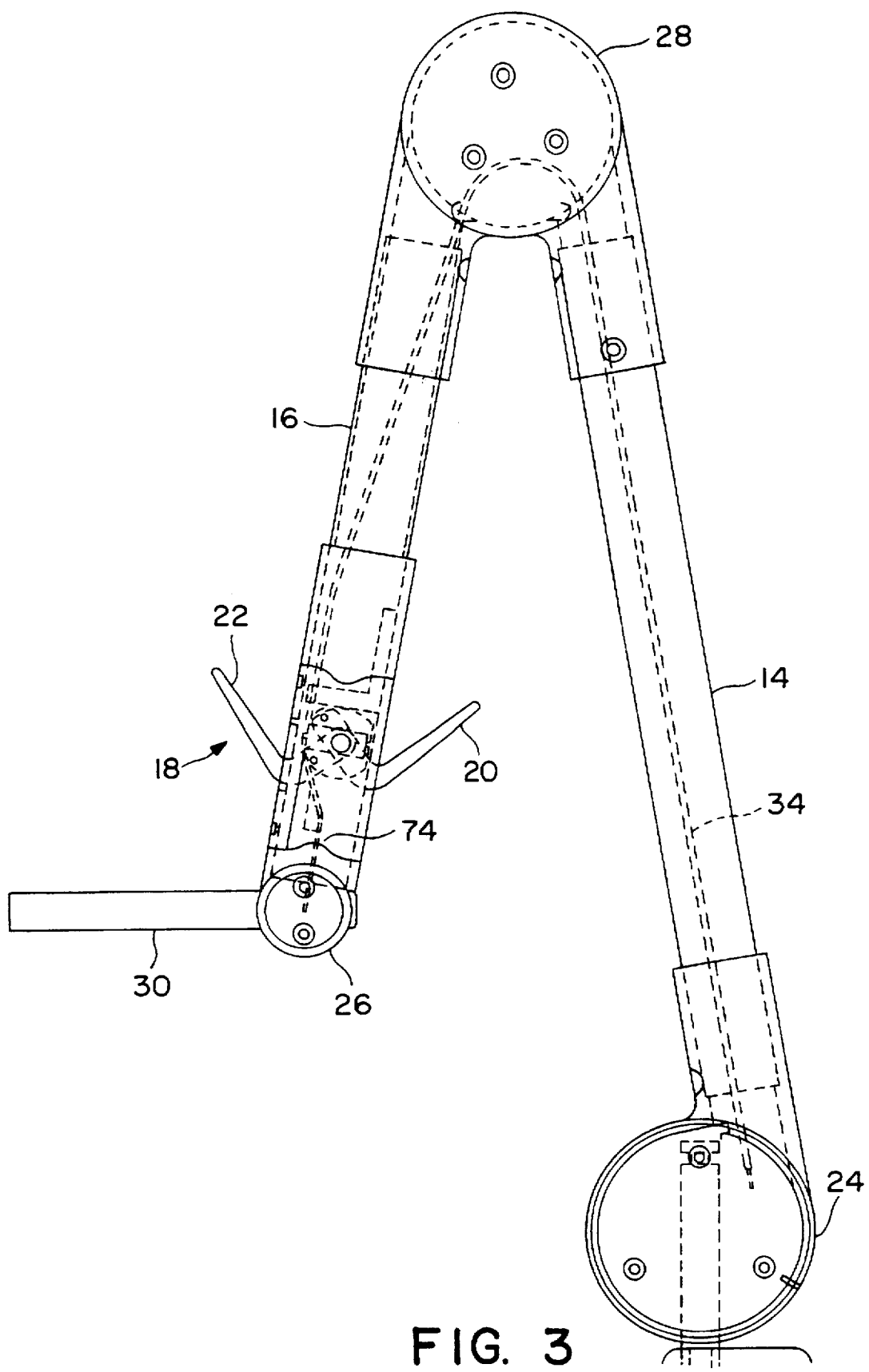
FIG. 3 is a side view showing hidden features of the FIG. 1 positioning unit.

Referring to FIGS. 1, 2 and 3, a positioning unit, constructed in accordance with the present invention, includes mounting means 10 for mounting the positioning unit to a stationary surface, such as a table top 12.

Also included in a positioning unit, constructed in accordance with the present invention, are a first arm 14 and a second arm 16.

A positioning unit, constructed in accordance with the present invention, further includes control means 18 for controlling, upon actuation by a single human hand, locking of first arm 14 and second arm 16 against movement of the first arm and the second arm and selective releasing of the first arm and the second arm to permit movement of the first arm and the second arm. For the embodiment of the present invention being described and illustrated by the drawing, control means 18, preferably, are positioned on second arm 16 and include first and second controllers 20 and 22 in the form of levers. It is important to note that this arrangement of first and second controllers 20 and 22 permits simultaneous actuation and release by a single human hand.

A positioning unit, constructed in accordance with the present invention, further includes a first joint 24, a second joint 26 and a third joint 28. Joint 24 couples first arm 14 to mounting means 10 for rotational movement of the first arm relative to the mounting means about a first vertical axis and pivotal movement of the first arm relative to the mounting means about a first horizontal axis. Joint 26 couples a payload, for example an ultrasound probe, normally attached to the end of a member 30 to second arm 16 for pivotal movement of the payload relative to the second arm about a second horizontal axis and rotational movement of the payload relative to the second arm about an axis perpendicular to the second horizontal axis. First arm 14 and second arm 16 are coupled together for relative pivotal movement between the first arm and the second arm about a third horizontal axis at joint 28.

Joint 24 has first locking and releasing means for preventing rotational movement of first arm 14 relative to mounting means 10 about the first vertical axis and pivotal movement of the first arm relative to the mounting means about the first horizontal axis and selectively permitting rotational movement of the first arm relative to the mounting means about the first vertical axis and pivotal movement of the first arm relative to the mounting means about the first horizontal axis.

As shown in FIGS. 4A and 4B, the first locking and releasing means of joint 24 include a first cam 32 which is connected to a first cable 34 which, as will be explained below, is connected to first controller 20. First cam 32, in response to first controller 20, moves between a first position shown in FIG. 4A and a second position shown in FIG. 4B.

The first locking and releasing means of joint 24 also include a first roller raceway 36, a first roller bearing 38 positioned between first cam 32 and the first roller raceway. In this position of first cam 32, there is clearance between first roller raceway 36, first roller bearing 38 and the first cam.

The first locking and releasing means of joint 24 further include a first resilient member, in the form of a Belleville washer 40, for urging first cam 32 to tightly captivate first roller bearing 38 between the first cam and first roller raceway 36 after the clearance between the first roller raceway, the first roller bearing and the first cam is taken up as the first cam moves from the first position of the first cam shown in FIG. 4A to the second position of the first cam shown in FIG. 4B. With further movement of first cam 32 toward the second position of the first cam, first roller bearing 38 undergoes rolling movement.

The first locking and releasing means of joint 24 further include means responsive to first cam 32 and first resilient member 40 for clamping first arm 14 to prevent rotational movement of the first arm about the first vertical axis and pivotal movement of the first arm about the first horizontal axis when the first cam is in first position of the first cam, as shown in FIG. 4A and releasing the first arm to permit rotational movement of the first arm about the first vertical axis and pivotal movement of the first arm about the first horizontal axis when the first cam is in the second position of the first cam, as shown in FIG. 4B. In particular, such means include a cup-shaped member 42 which urges a shaft 44, connected to first arm 14 and passing through cup-shaped member 42, to the left as viewed in FIG. 4A, so that shaft 44 is clamped between cup-shaped member 42 and a pulley sheath cylinder 46. Cup-shaped member 42 is urged to the left by a first pin 48 which is urged to the left by first resilient member 40. The urging to the left of first pin 48 is transmitted through a lock ring 50 and a washer 52 to cup-shaped member 42. Clamping of shaft 44 prevents rotation of first arm 14 about the first vertical axis.

With first cam 32 in the position shown in FIG. 4A, a circular member 54, to which first arm 14 is fixed and through which cable 34 passes and which is fixed to a second cup-shaped member 56, a first pulley 58, a second pulley 60 and pulley sheath cylinder 46 are all clamped together to prevent rotation of all of these parts about the first horizontal axis. In this way, first arm 14 is prevented from undergoing pivotal movement about the first horizontal axis.

As first cam 32 moves toward the second position of the first cam as shown in FIG. 4B in response to first cable 34 being drawn upward by actuation of first controller 20, the first cam pivots about first roller bearing 38 and moves first pin 48 to the right, as viewed in FIG. 4B, against the action of first resilient member 40, cup-shaped member 42 is free to move to the right releasing shaft 44 to permit rotation of first arm 14 about the first vertical axis. At the same time, the clamping of circular member 54, through which cable 34 passes and which is fixed to a second cup-shaped member 56, a first pulley 58, a second pulley 60 and pulley sheath cylinder 46 is removed and first arm 14, fixed to circular member 54, is permitted to undergo pivotal movement about the first horizontal axis.

When controller 20 is released, so that first cam 32 is no longer urged toward the second position of the first cam, as shown in FIG. 4B, first resilient member 40 urges the first cam back toward the first position of the first cam, as shown in FIG. 4A, until there is clearance between first roller raceway 36, first roller bearing 38 and the first cam. Shaft 44 then is clamped and prevents rotation of first arm 14 about the first vertical axis and pivotal movement about the first horizontal axis. An extension coil spring 62 urges first cam 32 back to the first position of the first cam as shown in FIG. 4A. A pair of compression coil springs 66, only one of which is shown in FIGS. 4A and 4B, urge first roller bearing 38 back to its initial position.

Joint 26 has second locking and releasing means for preventing pivotal movement of the payload relative to second arm 16 about the second horizontal axis and rotational movement of the payload relative to the second arm about the axis perpendicular to the second horizontal axis and selectively permitting pivotal movement of the payload relative to the second arm about the second horizontal axis and rotational movement of the payload relative to the second arm about the axis perpendicular to the second horizontal axis.

Figure 5A:
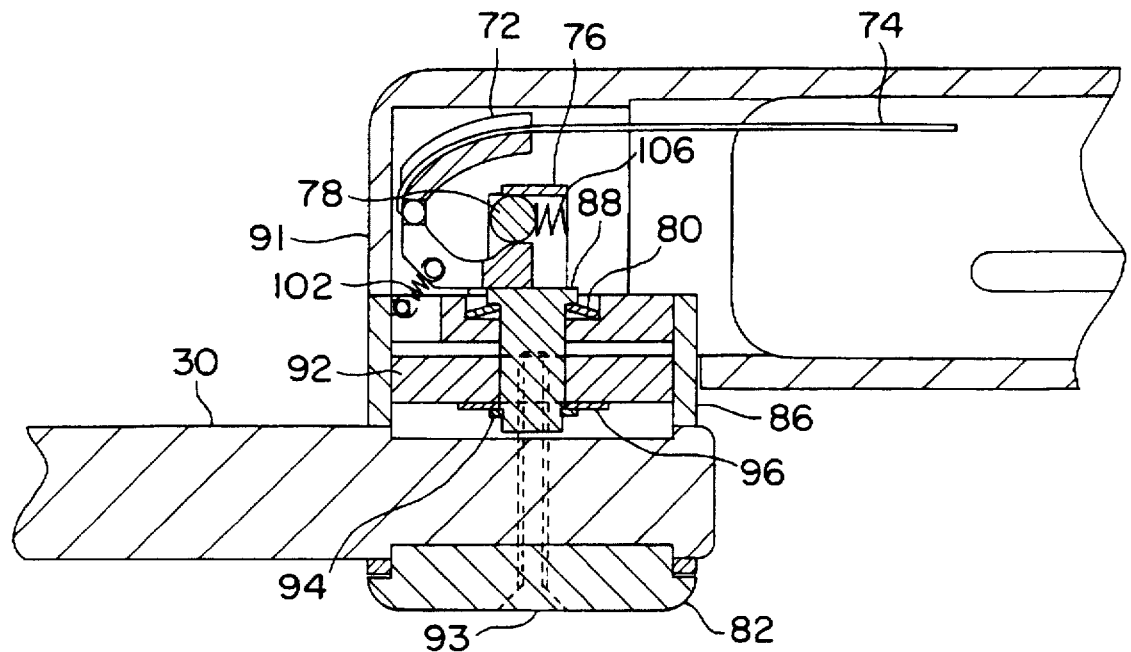
FIG. 5A and 5B are sectional views of a second joint of the FIG. 1 positioning unit in the locked condition and the released condition, respectively.
Figure 5B:
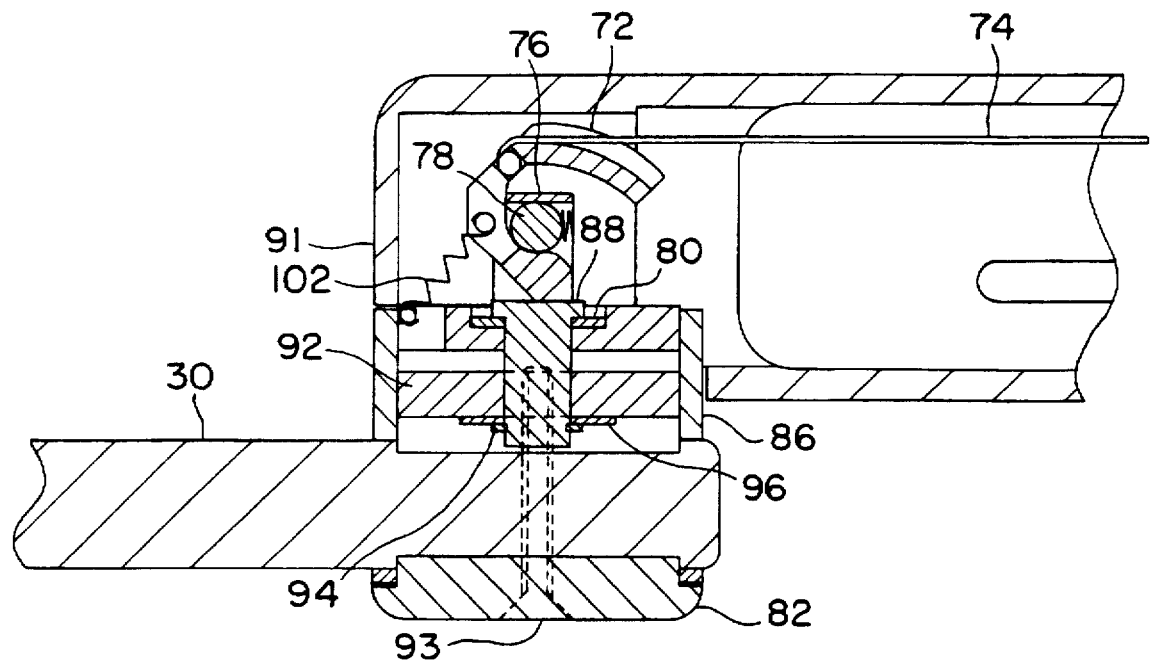

As shown in FIGS. 5A and 5B, the second locking and releasing means of joint 26 include a second cam 72 which is connected to a second cable 74 which, as will be explained below, is connected to second controller 22. Second cam 72, in response to second controller 22, moves between a first position shown in FIG. 5A and a second position shown in FIG. 5B.

The second locking and releasing means of joint 26 also include a second roller raceway 76, a second roller bearing 78 positioned between second cam 72 and the second roller raceway. In this position of second cam 72, there is clearance between second roller raceway 76, second roller bearing 78 and the second cam.

The second locking and releasing means of joint 26 further include a second resilient member, in the form of a Belleville washer 80, for urging second cam 72 to tightly captivate second roller bearing 78 between the second cam and second roller raceway 76 after the clearance between second roller raceway 76, the second roller bearing and the second cam is taken up as the second cam moves from the first position of the second cam shown in FIG. 5A to the second position of the second cam shown in FIG. 5B. With further movement of second cam 72 toward the second position of the second cam, second roller bearing 78 undergoes rolling movement.

The second locking and releasing means of joint 26 further include means responsive to second cam 72 and second resilient member 80 for clamping the payload to prevent pivotal movement of the payload relative to second arm 16 about the second horizontal axis and rotational movement of the payload relative to the second arm about the axis perpendicular to the second horizontal axis when the second cam is in first position of the second cam, as shown in FIG. 5A, and releasing the second arm to permit pivotal movement of the payload relative to the second arm about the second horizontal axis and rotational movement of the payload relative to the second arm about the axis perpendicular to the second horizontal axis when the second cam is in the second position of the second cam, as shown in FIG. 5B. In particular, such means include a cap member 82 which urges a shaft 30, connected to the payload and passing through a cylinder 86, upward as viewed in FIG. 5A, so that shaft 30 is clamped between cap member 82 and cylinder 86 and cylinder 86 is urged against an edge of a housing 91. In this way, cylinder 86 and, therefore, shaft 30 are prevented from pivoting about the second horizontal axis and shaft 30 is prevented from rotating about the axis perpendicular to the second horizontal axis.

Cap member 82 is urged upward by a second pin 88 which extends through a plate 92 to which the cap member is fastened by a pair of screws 93, only one of which is shown in FIGS. 5A and 5B. Second pin 88 is urged upward by second resilient member 80. The urging upward of second pin 88 is transmitted through a second lock ring 94 and a second washer 96 to plate 92 which, in turn, urges cap member 82 upward because the cap member is fastened to plate 92 by screws 93. Clamping of shaft 30 prevents pivotal movement of the payload relative to second arm 16 about the second horizontal axis and rotational movement of the payload about the axis perpendicular to the second horizontal axis.

As second cam 72 moves toward the second position of the second cam as shown in FIG. 5B in response to second cable 74 being drawn to the right by actuation of second controller 22, the second cam pivots about second roller bearing 78 and moves second pin 88 downward, as viewed in FIG. 5B, against the action of second resilient member 80 and cap member 82 is free to move downward releasing shaft 30 to permit rotation of the payload about the axis perpendicular to the second horizontal axis. At the same time, cylinder 86 is no longer urged to bear against an edge of a housing 91 and, therefore, is permitted to undergo pivotal movement about the second horizontal axis.

When controller 22 is released, so that second cam 72 is no longer urged toward the second position of the second cam, as shown in FIG. 5B, second resilient member 80 urges the second cam back toward the first position of the second cam, as shown in FIG. 5A, until there is clearance between second roller raceway 76, second roller bearing 78 and the second cam. Shaft 30 then is clamped and prevents rotation of the payload about the axis perpendicular to the second horizontal axis and pivotal movement about the second horizontal axis. An extension coil spring 102 urges second cam 72 back to the first position of the second cam as shown in FIG. 5A. A pair of compression coil springs 106, only one of which is shown in FIGS. 5A and 5B, urge second roller bearing 78 back to its initial position.

Figure 6:
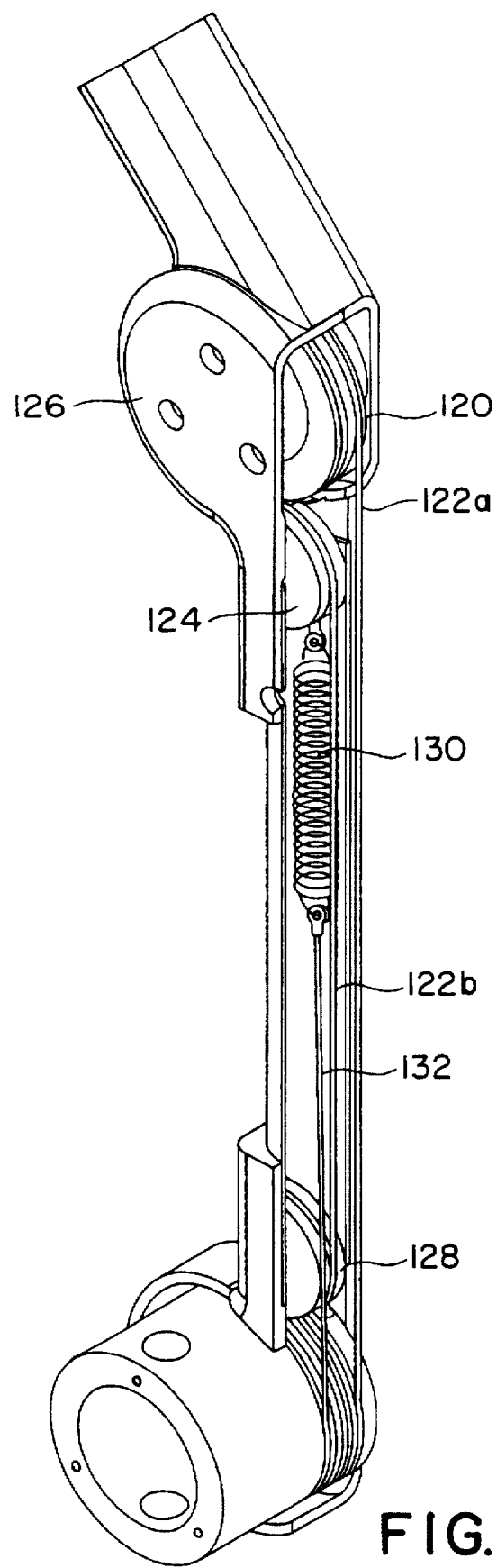
FIG. 6 is a perspective view, partially broken away, showing the mechanism by which a third joint of the FIG. 1 positioning unit is locked and released.

Joint 28 has third locking and releasing means for preventing relative pivotal movement between first arm 14 and second arm 16 about the third horizontal axis and selectively permitting relative pivotal movement between the first arm and the second arm about the third horizontal axis. Referring to FIGS. 4A, 4B and 6, the third locking and releasing means include a pulley 120 which is integral with second arm 16. A cable 122a is fixed at a first end to pulley 58 in the locking and releasing means of joint 24 and at a second end to pulley 120. A second cable 122b is fixed at a first end to pulley 120 and at a second end to pulley 60 in the first locking and releasing means of joint 24. Cable 122b bears against a cable guide 124 which is fixed to housing 126 of third joint 28 and against a cable guide 128. By restricting movement of pulley 120, movement of second arm 16 is restricted. When pulleys 58 and 60 of the first locking and releasing means of joint 24 are clamped, so that first arm 14 is locked against rotational movement about the first vertical axis and pivotal movement about the first horizontal axis, pulley 120 and, therefore, second arm 16 are locked against pivotal movement about the third horizontal axis because one end of cable 122a and one end of cable 122b are fixed to locked pulley 58 and locked pulley 60, respectively, and, with the other ends of cables 122a and 122b both fixed to pulley 120, there is in effect a single cable having both of its ends fixed to components which are locked against movement. When pulleys 58 and 60 of the first locking and releasing means of joint 24 are released, so that first arm 14 is released to permit rotational movement about the first vertical axis and pivotal movement about the first horizontal axis, pulley 120 and, therefore, second arm 16 are free to undergo pivotal movement about the third horizontal axis because one end of cable 122a and one end of cable 122b are fixed to release pulley 58 and released pulley 60, respectively, and, with the other ends of cables 122a and 122b both fixed to pulley 120, there is in effect a single cable having both of its ends fixed to components which are free to move. As is evident, for the embodiment of the invention being described, the third locking and releasing means in joint 28 are connected to the first locking and releasing means in joint 24, so that the effect of actuation and deactuation of first controller 20 on the third locking and releasing means in joint 28 is through the control of the first locking and releasing means in joint 24 which has been described above in connection with FIGS. 4A and 4B.

A spring 130, which provides a counterbalance or counterforce, to movement of the positioning unit, is connected at its upper end to cable guide 124 and by a cable 132 at the lower end of the spring to pulley sheath cylinder 46 about which cable 132 wraps. As second arm 16 pivots counterclockwise about the third horizontal axis, cable 132, connected to the lower end of spring 130, wraps around pulley sheath cylinder 46 stretching the spring.

A positioning unit, constructed in accordance with the present invention, further includes connecting means for connecting the control means to the first locking and releasing means to release the first locking and releasing means upon actuation of the control means and lock the first locking and releasing means upon deactuation of the control means, the second locking and releasing means to release the second locking and releasing means upon actuation of the control means and lock the second locking and releasing means upon deactuation of the control means, and the third locking and releasing means to release the third locking and releasing means upon actuation of the control means and lock the third locking and releasing means upon deactuation of the control means. As shown in FIG. 3, the connecting means include first cable 34 extending from first controller 20 to the first locking and releasing means in joint 24 and the third locking and releasing means in joint 28 and second cable 74 extending from second controller 22 to the second locking and releasing means in joint 26. The effect of the actuation and deactuation of controller 20, as conducted through first cable 34 to the first locking and releasing means in joint 24 and the third locking and releasing means in joint 28, and the effect of the actuation and deactuation of controller 22, as conducted through second cable 74 to the second locking and releasing means in joint 26, has already been described in connection with the description of the first locking and releasing means in joint 24 shown in FIGS. 4A and 4B, the second locking and releasing means in joint 26 shown in FIGS. 5A and 5B and the third locking and releasing means in joint 28 shown in FIGS. 4A, 4B and 6.

Figure 7:
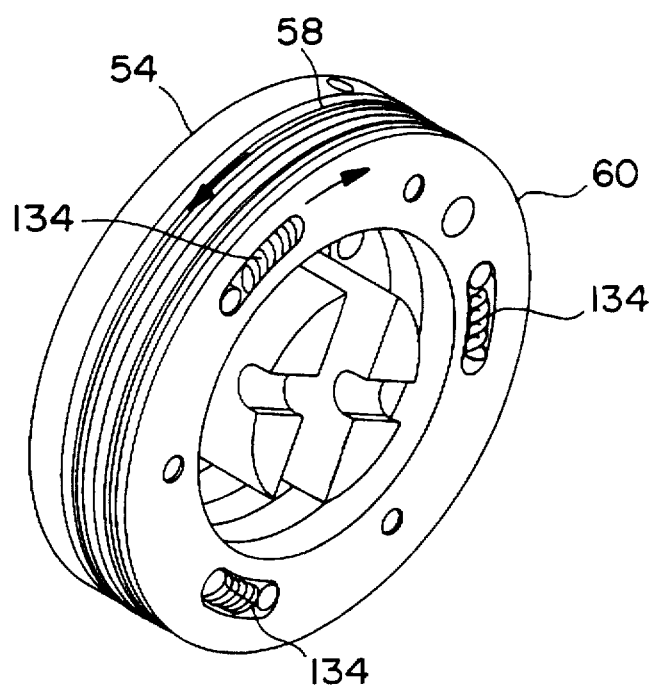
FIG. 7 is a perspective view of a portion of the joint of FIGS. 4A and 4B.

Referring to FIG. 7, a plurality of springs 134 are shown disposed between pulleys 58 and 60. These springs urge pulleys 58 and 60 to rotate in opposite directions, as indicated by the arrows, so that when the first locking and releasing means in joint 24 are released and pulleys 58 and 60 are not clamped, the two pulleys can rotate in opposite directions to take up any slack in cable 122.

Although the present invention has been described with reference to exemplary embodiments, it is not limited thereto. Rather, the appended claims should be construed to include other variants and embodiments of the invention which may be made by those of ordinary skill in the art without departing from the true spirit and scope of the present invention.

What is claimed:

1. A positioning unit comprising:
   mounting means for mounting said positioning unit to a stationary surface;
   a first arm;
   a second arm;
   control means for controlling, upon actuation by a single human hand:
   (a) locking of said first arm and said second arm against movement of said first arm and said second arm, and
   (b) selective releasing of said first arm and said second arm to permit movement of said first arm and said second arm;
   a first joint for coupling said first arm to said mounting means for:
   (a) rotational movement of said first arm relative to said mounting means about a first vertical axis, and
   (b) pivotal movement of said first arm relative to said mounting means about a first horizontal axis,
   and having first locking and releasing means for:
   (a) preventing:
      (1) rotational movement of said first arm relative to said mounting means about said first vertical axis, and
      (2) pivotal movement of said first arm relative to said mounting means about said first horizontal axis, and
   (b) selectively permitting:
      (1) rotational movement of said first arm relative to said mounting means about said first vertical axis, and
      (2) pivotal movement of said first arm relative to said mounting means about said first horizontal axis;
   a second joint for coupling a payload to said second arm for:
   (a) pivotal movement of the payload relative to said second arm about a second horizontal axis, and
   (b) rotational movement of the payload relative to said second arm about an axis perpendicular to said second horizontal axis,
   and having second locking and releasing means for:
   (a) preventing:
      (1) pivotal movement of the payload relative to said second arm about said second horizontal axis, and
      (2) rotational movement of the payload relative to said second arm about said axis perpendicular to said second horizontal axis, and
   (b) selectively permitting:
      (1) pivotal movement of the payload relative to said second arm about said second horizontal axis, and
      (2) rotational movement of the payload relative to said second arm about said axis perpendicular to said second horizontal axis;
   a third joint at which said first arm and said second arm are coupled together for relative pivotal movement between said first arm and said second arm about a third horizontal axis and having third locking and releasing means for:
   (a) preventing relative pivotal movement between said first arm and said second arm about said third horizontal axis, and
   (b) selectively permitting relative pivotal movement between said first arm and said second arm about said third horizontal axis; and
   connecting means for connecting said control means to:
   (a) said first locking and releasing means to:
      (1) release said first locking and releasing means upon actuation of said control means, and
      (2) lock said first locking and releasing means upon deactuation of said control means,
   (b) said second locking and releasing means to:
      (1) release said second locking and releasing means upon actuation of said control means, and
      (2) lock said second locking and releasing means upon deactuation of said control means, and
   (c) said third locking and releasing means to:
      (1) release said third locking and releasing means upon actuation of said control means, and
      (2) lock said third locking and releasing means upon deactuation of said control means.

2. A positioning unit according to claim 1 wherein said control means are positioned on said second arm.

3. A positioning unit according to claim 2 wherein said control means include first and second controllers and said connecting means connect:
   (a) said first controller to said first locking and releasing means and said third locking and releasing means, and
   (b) said second controller to said second locking and releasing means.

4. A positioning unit according to claim 3 wherein said first locking and releasing means and said third locking and releasing means are actuated and deactuated simultaneously by said first controller.

5. A positioning unit according to claim 4 wherein said third locking and releasing means include:
   (a) a pulley fixed to and movable with said second arm,
   (b) a first cable fixed at a first end to said pulley and fixed at a second end to said first locking and releasing means and a second cable fixed at a first end to said pulley and fixed at a second end to said first locking and releasing means, so that:
      (1) when said first locking and releasing means are locked, said cables are prevented from moving and said pulley and said second arm are locked against pivotal movement relative to said first arm about said third horizontal axis, and
      (2) when said first locking and releasing means are released, said cables are free to move and said pulley and said second arm are free to undergo pivotal movement relative to said first arm about said third horizontal axis.

6. A positioning unit according to claim 3 wherein said connecting means include:
   (a) a first cable extending from said first controller to said first locking and releasing means and said third locking and releasing means, and
   (b) a second cable extending from said second controller to said second locking and releasing means.

7. A positioning unit according to claim 6 wherein:
   (a) said first locking and releasing means include:
      (1) a first cam connected to said first cable and responsive to said first controller for movement between a first position and a second position,
      (2) a first roller raceway,
      (3) a first roller bearing positioned between said first cam and said first roller raceway,
      (4) a first resilient member for urging said first cam to tightly captivate said first roller bearing between said first cam and said first roller raceway for rolling movement of said first roller bearing as said first cam moves from said first position of said first cam to said second position of said first cam, and
      (5) means responsive to said first cam and said first resilient member for:
         (i) clamping said first arm to prevent rotational movement of said first arm about said first vertical axis and pivotal movement of said first arm about said first horizontal axis when said first cam is in said first position of said first cam, and
         (ii) releasing said first arm to permit rotational movement of said first arm about said first vertical axis and pivotal movement of said first arm about said first horizontal axis when said first cam is in said second position of said first cam, and (b) said second locking and releasing means include:
      (1) a second cam connected to said second cable and responsive to said second controller for movement between a first position and a second position,
      (2) a second roller raceway,
      (3) a second roller bearing positioned between said second cam and said second roller raceway,
      (4) a second resilient member for urging said second cam to tightly captivate said second roller bearing between said second cam and said second roller raceway for rolling movement of said second roller bearing as said second cam moves from said first position of said second cam to said second position of said second cam, and
      (5) means responsive to said second cam and said second resilient member for:
         (i) clamping the payload to prevent rotational movement of the payload about said axis perpendicular to said second horizontal axis and pivotal movement of the payload about said second horizontal axis when said second cam is in said first position of said second cam, and
         (ii) releasing the payload to permit rotational movement of the payload about said axis perpendicular to said second horizontal axis and pivotal movement of the payload about said second horizontal axis when said second cam is in said second position of said second cam.

8. A positioning unit according to claim 7 wherein said first locking and releasing means and said third locking and releasing means are actuated and deactuated simultaneously by said first controller.

9. A positioning unit according to claim 8 wherein said third locking and releasing means include:
   (a) a pulley fixed to and movable with said second arm, and
   (b) a third cable fixed at a first end to said pulley and fixed at a second end to said first locking and releasing means and a fourth cable fixed at a first end to said pulley and fixed at a second end to said first locking and releasing means, so that:
      (1) when said first locking and releasing means are locked, said third cable and said fourth cable are prevented from moving and said pulley and said second arm are locked against pivotal movement relative to said first arm about said third horizontal axis, and
      (2) when said first locking and releasing means are released, said third cable and said fourth cable are free to move and said pulley and said second arm are free to undergo pivotal movement relative to said first arm about said third horizontal axis.

* * * * *